United States Patent

Mockel et al.

(12)

(10) Patent No.: US 6,759,218 B2
(45) Date of Patent: Jul. 6, 2004

(54) NUCLEOTIDE SEQUENCES CODING FOR THE GLBO GENE

(75) Inventors: Bettina Mockel, Dusseldorf (DE); Achim Marx, Bielefeld (DE); Walter Pfefferle, Halle (DE)

(73) Assignee: Degussa-AG, Dusseldorf (DE)

( * ) Notice: Subject to any disclaimer, the term of this patent is extended or adjusted under 35 U.S.C. 154(b) by 0 days.

(21) Appl. No.: 10/139,520

(22) Filed: May 7, 2002

(65) Prior Publication Data

US 2003/0166173 A1 Sep. 4, 2003

Related U.S. Application Data

(63) Continuation-in-part of application No. 09/813,932, filed on Mar. 22, 2001, now abandoned, which is a continuation-in-part of application No. 09/585,642, filed on Jun. 2, 2000, now abandoned.

(51) Int. Cl.[7] .......................... C12P 13/04; C12N 1/20; C12N 15/00; C12D 13/08
(52) U.S. Cl. .................. 435/106; 435/252.32; 435/115; 435/320.1
(58) Field of Search ........................... 435/106, 252.32, 435/115, 320.1, 69.1

(56) References Cited

FOREIGN PATENT DOCUMENTS

| EP | 0 197 335 A | | 10/1986 |
|---|---|---|---|
| EP | 1 108 790 A | | 6/2001 |
| WO | WO 92/03546 A | | 3/1992 |
| WO | WO 92/03546 | * | 3/1992 |
| WO | WO 93/25697 A | | 12/1993 |
| WO | WO 01 00805 A | | 1/2001 |

OTHER PUBLICATIONS

Database EMBL [Online] accession: AF213450; 053197, Mar. 3, 2000; Pathania R. et al., "Mycobacterium bovis oxygen–binding protein (glb0) gene, complete cds." XP002183809.
Database EMBL [Online] accession: AX127151; AX114121, May 10, 2001, Nakagawa S. et al., "Sequence 7067 from patent EP1108790".
EPO Search Report of PCT/EP01/04792 dated Nov. 30, 2001.

* cited by examiner

Primary Examiner—Rebecca E. Prouty
Assistant Examiner—Malgorzata A Walicka
(74) Attorney, Agent, or Firm—Smith, Gambrell & Russell (57) ABSTRACT

The present invention provides an isolated polynucleotide containing a polynucleotide sequence selected from the group a) polynucleotide which is at least 70% identical to a polynucleotide which codes for a polypeptide containing the amino acid sequence of SEQ ID no. 2, b) polynucleotide which codes for a polypeptide which contains an amino acid sequence which is at least 70% identical to the amino acid sequence of SEQ ID no. 2, c) polynucleotide which is complementary to the polynucleotides of a) or b), and d) polynucleotide containing at least 15 successive nucleotides of the polynucleotide sequence of a), b) or c), and a process for the fermentative production of L-amino acids with enhancement of the glbO gene which codes for the haemoglobin-like protein and the use of the above polynucleotides as a primer or hybridization probe.

20 Claims, 2 Drawing Sheets

Figure 1: Map of plasmid pEC-K18mob2

Figure 2: Map of plasmid pEC-K18mob2glbOexp

NUCLEOTIDE SEQUENCES CODING FOR THE GLBO GENE

RELATED APPLICATIONS

This application is a continuation-in-part of U.S. patent application Ser. No. 09/813,932 filed Mar. 22, 2001, now abandoned, which is a continuation-in-part of U.S. patent application Ser. No. 09/585,642 filed Jun. 2, 2000, now abandoned, which are both incorporated herein, in their entirety, by reference.

FIELD OF THE INVENTION

The invention provides nucleotide sequences coding for the glbO gene and a process for the fermentative production of L-amino acids, in particular L-lysine, using coryneform bacteria in which the glbO gene is amplified or enhanced. All references cited herein are expressly incorporated by reference. Incorporation by reference is also designated by the term "I.B.R." following any citation.

PRIOR ART

L-amino acids, in particular L-lysine, are used in human medicine and in the pharmaceuticals industry, but especially in animal nutrition.

It is known that L-amino acids are produced by fermentation of strains of coryneform bacteria, in particular Corynebacterium glutamicum. Due to their great significance, efforts are constantly being made to improve the production process. Improvements to the process may relate to measures concerning fermentation technology, for example stirring and oxygen supply, or to the composition of the nutrient media, such as for example sugar concentration during fermentation, or to working up to yield the product by, for example, ion exchange chromatography, or to the intrinsic performance characteristics of the microorganism itself.

The performance characteristics of these microorganisms are improved using methods of mutagenesis, selection and mutant selection. In this manner, strains are obtained which are resistant to antimetabolites, such as for example the lysine analogue S-(2-aminoethyl)cysteine, or are auxotrophic for regulatory significant metabolites and produce L-lysine.

For some years, methods of recombinant DNA technology have also been used to improve strains of Corynebacterium which produce L-amino acids by amplifying individual biosynthesis genes for L-amino acids and investigating the effect on L-amino acid production.

Review articles on this subject may be found inter alia in Kinoshita ("Glutamic Acid Bacteria", in: Biology of Industrial Microorganisms, Demain and Solomon (Eds.), Benjamin Cummings, London, UK, 1985, 115–142) I.B.R., Hilliger (BioTec 2, 40–44 (1991)), Eggeling (Amino Acids 6:261–272 (1994)) I.B.R., Jetten and Sinskey (Critical Reviews in Biotechnology 15, 73–103 (1995)) I.B.R. and Sahm et al. (Annuals of the New York Academy of Science 782, 25–39 (1996)) I.B.R.

OBJECT OF THE INVENTION

An object of the invention is to provide new measures for improved fermentative preparation of L-amino acids, in particular L-lysine. Amino acids, in particular L-lysine, are used in human medicine, in the pharmaceuticals industry and, in particular, in animal nutrition. Therefore, there is a general interest in providing new improved processes for the preparation of amino acids, in particular L-lysine. When L-lysine or lysine are mentioned in the following, not only the base but also the salts, such as e.g. lysine monohydrochloride or lysine sulfate, are also meant by this.

Any subsequent mention of L-amino acids or amino acids should be taken to mean one or more amino acids, including the salts thereof, selected from the group comprising L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-Lysine is particularly preferred.

Any subsequent mention of L-lysine or lysine should be taken to mean not only the base, but also salts, such as for example lysine monohydrochloride or lysine sulfate.

SUMMARY OF THE INVENTION

The new DNA sequence of C. glutamicum which codes for the globin oxygen gene (glbO) and which as a constituent of the present invention is SEQ ID NO 1 and related sequences. The amino acid sequence of the corresponding gene product of the glbO gene has furthermore been derived from the present DNA sequence. The resulting amino acid sequence of the glbO gene product is SEQ ID NO 2 and related sequences.

BRIEF DESCRIPTION OF THE DRAWINGS

The present invention will be further understood with reference to the drawing offered here for illustration only and not in limitation of this invention.

Figure 1:
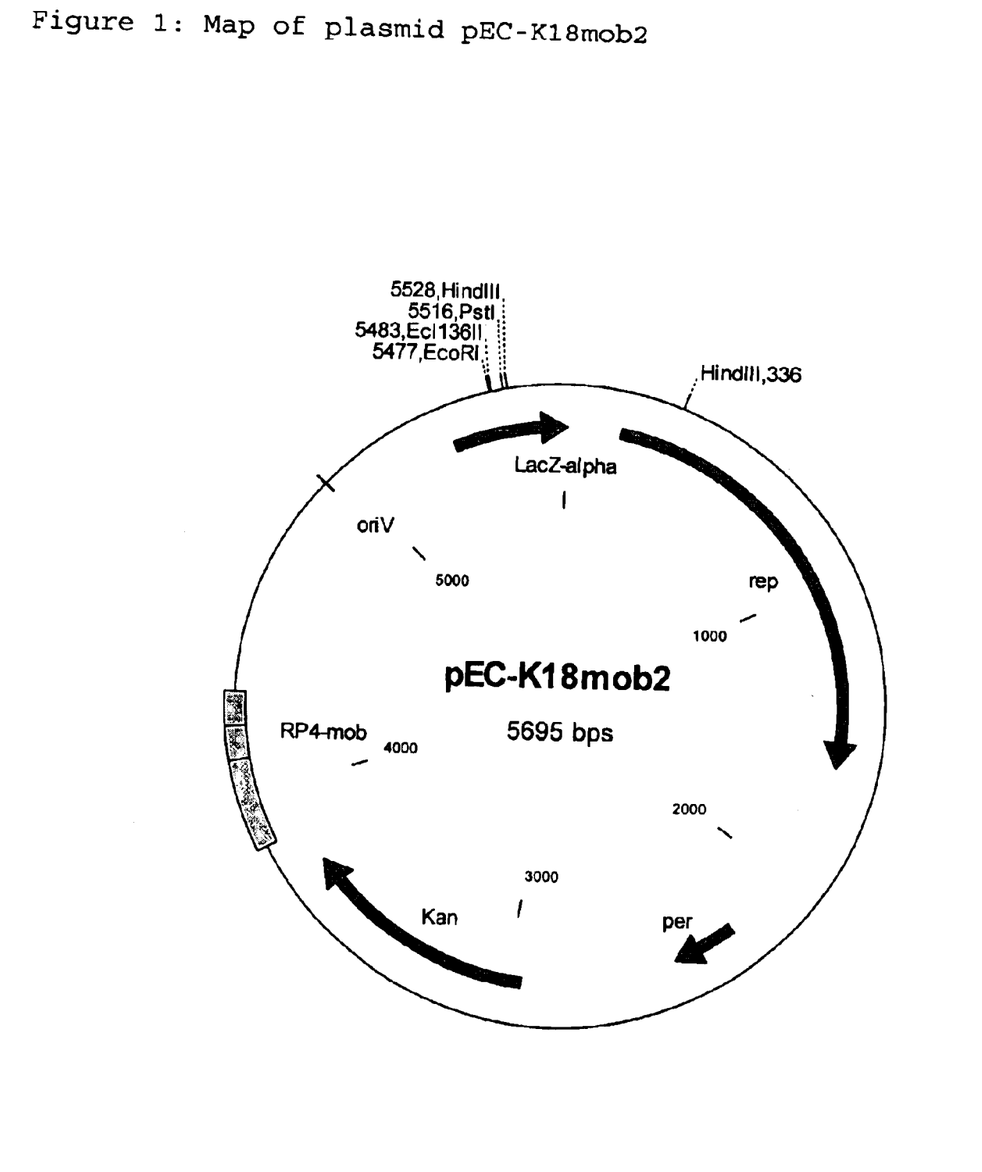
FIG. 1 is a map of the plasmid pEC-K18mob2.
Figure 2:
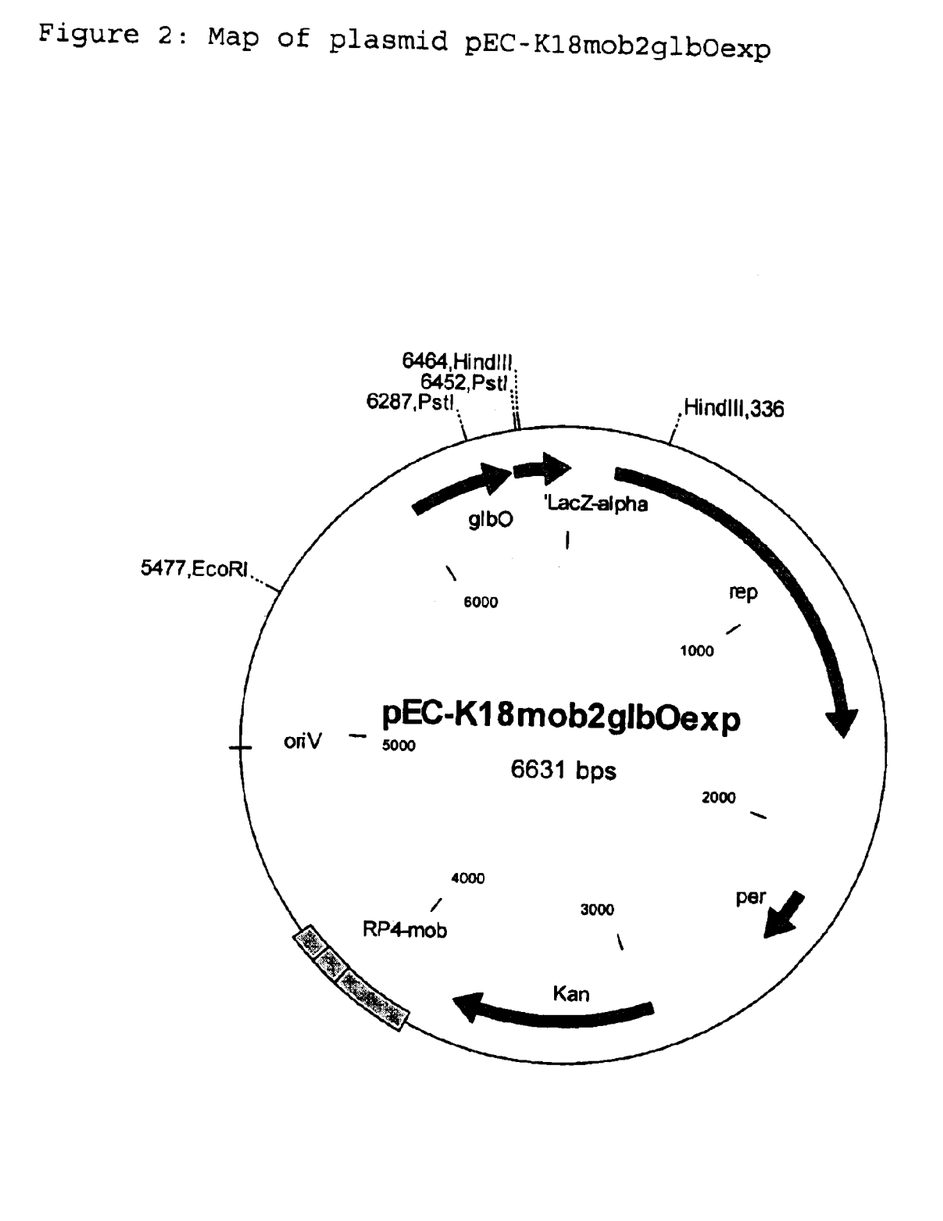
FIG. 2 is a map of the plasmid pEC-K18mob2glbOexp.

The abbreviations and names are defined as follows. The stated base pair figures are approximate values obtained within the framework of measurement reproducibility.

| | |
|---|---|
| per: | Gene for controlling copy number from pGA1 |
| oriV: | ColE1-like origin from pMB1 |
| rep: | Plasmid-coded replication region from C. glutamicum plasmid pGA1 |
| RP4mob: | RP4 mobilization site |
| lacZ-alpha: | lacZ gene fragment from E. coli |
| Kan: | Kanamycin resistance gene |
| glbO: | glbO gene from C. glutamicum |
| EcoRI: | Restriction site of the restriction enzyme EcoRI |
| HindIII: | Restriction site of the restriction enzyme HindIII |
| PstI: | Restriction site of the restriction enzyme PstI |
| Ecl136II: | Restriction site of the restriction enzyme Ecl136II |

DETAILED DESCRIPTION OF THE INVENTION

The invention provides an isolated polynucleotide from coryneform bacteria containing a polynucleotide sequence selected from the group a) polynucleotide which is at least 70% identical to a polynucleotide which codes for a polypeptide containing the amino acid sequence of SEQ ID no. 2, b) polynucleotide which codes for a polypeptide which contains an amino acid sequence which is at least 70% identical to the amino acid sequence of SEQ ID no. 2, c) polynucleotide which is complementary to the polynucleotides of a) or b), and d) polynucleotide containing at least 15 successive nucleotides of the polynucleotide sequence of a), b) or c), wherein the polypeptide preferably exhibits the activity of the haemoglobin-like protein.

The present invention also provides a polynucleotide which is a preferably recombinant DNA replicable in coryneform bacteria.

The present invention also provides a polynucleotide which is an RNA.

The present invention also provides a polynucleotide as described above, wherein it preferably comprises a replicable DNA containing:

(i) the nucleotide sequence shown in SEQ ID no. 1, or (ii) at least one sequence which matches the sequence (i) within the degeneration range of the genetic code, or (iii) at least one sequence which hybridizes with the complementary sequence to sequence (i) or (ii) and optionally (iv) functionally neutral sense mutations in (i).

The relative degree of substitution or mutation in the polynucleotide or amino acid sequence to produce a desired percentage of sequence identity can be established or determined by well-known methods of sequence analysis. These methods are disclosed and demonstrated in Bishop, et al. "DNA & Protein Sequence Analysis (A Practical Approach"), Oxford Univ. Press, Inc. (1997) I.B.R. and by Steinberg, Michael "Protein Structure Prediction" (A Practical Approach), Oxford Univ. Press, Inc. (1997) I.B.R. Hybridization of complementary sequences can occur at varying degrees of stringency. Sambrook et al.: Molecular Cloning, A Laboratory Manual (Cold Spring Harbor Laboratory Press, 1989) I.B.R.

Hybridization of complementary sequences can occur at varying degrees of stringency. Sambrook et al.: Molecular Cloning, A Laboratory Manual (Cold Spring Harbor Laboratory Press, 1989) I.B.R. Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) I.B.R. and in Liebl et al. (International Journal of Systematic Bacteriology (1991) 41: 255–260) I.B.R.

Comprehensive descriptions can be found in known textbooks of genetics and molecular biology, such as e.g. that by Hagemann ("Allgemeine Genetik" [General Genetics], Gustav Fischer Verlag, Stuttgart, 1986) I.B.R.

Possible mutations are transitions, transversions, insertions and deletions. Depending on the effect of the amino acid exchange on the enzyme activity, missense mutations or nonsense mutations are referred to. Insertions or deletions of at least one base pair in a gene lead to frame shift mutations, as a consequence of which incorrect amino acids are incorporated or translation is interrupted prematurely. Deletions of several codons typically lead to a complete loss of the enzyme activity.

Instructions on generation of such mutations are prior art and can be found in known textbooks of genetics and molecular biology, such as e.g. the textbook by Knippers ("Molekulare Genetik"[Molecular Genetics], 6th edition, Georg Thieme Verlag, Stuttgart, Germany, 1995) I.B.R., that by Winnacker ("Gene und Klone"[Genes and Clones], VCH Verlagsgesellschaft, Weinheim, Germany, 1990) I.B.R. or that by Hagemann ("Allgemeine Genetik"[General Genetics], Gustav Fischer Verlag, Stuttgart, 1986) I.B.R.

The invention also provides a vector containing one of the stated polynucleotides and coryneform bacteria acting as host cell which contain the vector or in which the glbO gene is amplified.

The present invention also provides a vector containing the polynucleotide according to the invention, and coryneform bacteria acting as host cell which contain the vector or in which the glbO gene is enhanced.

The present invention also provides polynucleotides which substantially consist of a polynucleotide sequence, which are obtainable by screening by means of hybridization of a suitable gene library, which contains the complete gene having the polynucleotide sequence according to SEQ ID no. 1, with a probe which contains the sequence of the stated polynucleotide according to SEQ ID no. 1, or a fragment thereof, and isolation of the stated DNA sequence.

Polynucleotides containing the sequences according to the invention are suitable as hybridization probes for RNA, cDNA and DNA in order to isolate full length cDNA which code for the haemoglobin-like protein (glbO) and to isolate such cDNA or genes, the sequence of which exhibits a high level of similarity with that of the gene for the haemoglobin-like protein.

Polynucleotides which contain the sequences according to the invention are furthermore suitable as primers for the production of DNA of genes which code for the haemoglobin-like protein by the polymerase chain reaction (PCR).

Such oligonucleotides acting as probes or primers contain at least 30, preferably at least 20, very particularly preferably at least 15 successive nucleotides. Oligonucleotides having a length of at least 40 or 50 nucleotides are also suitable.

"Isolated" means separated from its natural environment.

"Polynucleotide" generally relates to polyribonucleotides and polydeoxyribonucleotides, wherein the RNA or DNA may be unmodified or modified.

"Polypeptides" are taken to mean peptides or proteins which contain two or more amino acids connected by peptide bonds.

The polypeptides according to the invention include a polypeptide according to SEQ ID no. 2, in particular those having the biological activity of the haemoglobin-like protein and also those which are at least 70% identical to the polypeptide according to SEQ ID no. 2 and which preferably exhibit at least 80% and in particular at least 90% to 95% identity to the polypeptide according to SEQ ID no. 2 and exhibit the stated activity.

The invention furthermore relates to a process for the fermentative production of L-amino acids, in particular L-lysine, using coryneform bacteria, which in particular already produce an L-amino acid and in which the nucleotide sequences which code for the glbO gene are enhanced, in particular over-expressed.

In this connection, the term "amplification" describes the increase in the intracellular activity of one or more enzymes in a microorganism, which enzymes are coded by the corresponding DNA, for example by increasing the copy number of the gene or genes, by using a strong promoter or a gene which codes for a corresponding enzyme having elevated activity and optionally by combining these measures.

The microorganisms, provided by the present invention, may produce L-amino acids, in particular L-lysine, from glucose, sucrose, lactose, fructose, maltose, molasses, starch, cellulose or from glycerol and ethanol. The microorganisms may comprise representatives of the coryneform bacteria in particular of the genus Corynebacterium. Within the genus Corynebacterium, the species *Corynebacterium glutamicum* may in particular be mentioned, which is known in specialist circles for its ability to produce L-amino acids.

Suitable strains of the genus Corynebacterium, in particular of the species *Corynebacterium glutamicum*, are for example the known wild type strains

*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Corynebacterium melassecola* ATCC17965
*Brevibacterium flavum* ATCC14067
*Brevibacterium lactofermentum* ATCC13869 and
*Brevibacterium divaricatum* ATCC14020
and L-lysine producing mutants or strains produced therefrom, such as for example
*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463
*Corynebacterium glutamicum* FERM-P 6464 and
*Corynebacterium glutamicum* DSM 5715.

The novel glbO gene which codes for the haemoglobin-like protein from *C. glutamicum* was isolated.

The glbO gene or also other genes from *C. glutamicum* are isolated by initially constructing a gene library of this microorganism in *E. coli*. The construction of gene libraries is described in generally known textbooks and manuals. Examples which may be mentioned are the textbook by Winnacker, Gene und Klone, Eine Einfuhrung in die Gentechnologie (Verlag Chemie, Weinheim, Germany, 1990) I.B.R. or the manual by Sambrook et al., Molecular Cloning, A Laboratory Manual (Cold Spring Harbor Laboratory Press, 1989) I.B.R. One very well known gene library is that of *E. coli* K-12 strain W3110, which was constructed by Kohara et al. (Cell 50, 495–508 (1987)) I.B.R. in λ-vectors. Bathe et al. (Molecular and General Genetics, 252:255–265, 1996) I.B.R. describe a gene library of *C. glutamicum* ATCC 13032, which was constructed using the cosmid vector SuperCos I (Wahl et al., 1987, Proceedings of the National Academy of Sciences USA, 84:2160–2164 I.B.R.) in *E. coli* K-12 strain NM554 (Raleigh et al., 1988, Nucleic Acids Research 16:1563–1575 I.B.R.). Börmann et al. (Molecular Microbiology 6(3), 317–326, 1992)) I.B.R. also describe a gene library of *C. glutamicum* ATCC 13032, using cosmid pHC79 (Hohn and Collins, Gene 11, 291–298 (1980) I.B.R.). A gene library of *C. glutamicum* in *E. coli* may also be produced using plasmids such as pBR322 (Bolivar, Life Sciences, 25, 807–818 (1979)) or pUC9 (Vieira et al., 1982, Gene, 19:259–268 I.B.R.). Suitable hosts are in particular those *E. coli* strains with restriction and recombination defects. One example of such a strain is the strain DH5αMCR, which has been described by Grant et al. (Proceedings of the National Academy of Sciences USA, 87 (1990) 4645–4649) I.B.R. The long DNA fragments cloned with the assistance of cosmids may then in turn be subcloned in usual vectors suitable for sequencing and then be sequenced, as described, for example, in Sanger et al. (Proceedings of the National Academy of Sciences of the United States of America, 74:5463–5467, 1977) I.B.R.

The novel DNA sequence from *C. glutamicum* which codes for the glbO gene was obtained and, as SEQ ID no. 1, is provided by the present invention. The amino acid sequence of the corresponding protein was furthermore deduced from the above DNA sequence using the methods described above. SEQ ID no. 2 shows the resultant amino acid sequence of the product of the glbO gene.

Coding DNA sequences arising from SEQ ID no. 1 due to the degeneracy of the genetic code are also provided by the present invention. Conservative substitutions of amino acids in proteins, for example the substitution of glycine for alanine or of aspartic acid for glutamic acid, are known in specialist circles as "sense mutations", which result in no fundamental change in activity of the protein, i.e. they are functionally neutral. It is furthermore known that changes to the N and/or C terminus of a protein do not substantially impair or may even stabilize the function thereof. The person skilled in the art will find information in this connection inter alia in Ben-Bassat et al. (Journal of Bacteriology 169:751–757 (1987)) I.B.R., in O'Regan et al. (Gene 77:237–251 (1989)) I.B.R., in Sahin-Toth et al. (Protein Sciences 3:240–247 (1994)) I.B.R., in Hochuli et al. (Bio/Technology 6:1321–1325 (1988)) I.B.R. and in known textbooks of genetics and molecular biology. Amino acid sequences arising in a corresponding manner from SEQ ID no. 2 and DNA sequences which code for these amino acid sequences are also provided by the present invention.

It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751–757 (1987)) I.B.R., in O'Regan et al. (Gene 77:237–251 (1989)) I.B.R., in Sahin-Toth et al. (Protein Sciences 3:240–247 (1994)) I.B.R., in Hochuli et al. (Bio/Technology 6:1321–1325 (1988)) I.B.R. and in known textbooks of genetics and molecular biology. Amino acid sequences which result in a corresponding manner from SEQ ID NO 2 are also a constituent of the invention.

DNA sequences which hybridize with SEQ ID no. 1 or parts of SEQ ID no. 1 are similarly provided by the invention. Finally, DNA sequences produced by the polymerase chain reaction (PCR) using primers obtained from SEQ ID no. 1 are also provided by the present invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) I.B.R. and in Liebl et al. (International Journal of Systematic Bacteriology (1991) 41: 255–260) I.B.R. Instructions for amplification of DNA sequences with the aid of the polymerase chain reaction (PCR) can be found by the expert, inter alia, in the handbook by Gait: Oligonukleotide synthesis: a practical approach (IRL Press, Oxford, UK, 1984) I.B.R. and in Newton and Graham: PCR (Spektrum Akademischer Verlag, Heidelberg, Germany, 1994) I.B.R.

The inventors discovered that coryneform bacteria produce L-amino acids, in particular L-lysine, in an improved manner once the glbO has been overexpressed.

Overexpression may be achieved by increasing the copy number of the corresponding genes or by mutating the promoter and regulation region or the ribosome-binding site located upstream from the structural gene. Expression cassettes incorporated upstream from the structural gene act in the same manner. It is additionally possible to increase expression during fermentative L-amino acid production by means of inducible promoters. Expression is also improved by measures to extend the lifetime of the mRNA. Enzyme activity is moreover amplified by preventing degradation of the enzyme protein. The genes or gene constructs may either be present in plasmids in a variable copy number or be integrated in the chromosome and amplified. Alternatively, overexpression of the genes concerned may also be achieved by modifying the composition of the nutrient media and culture conditions.

The person skilled in the art may find instructions for identifying DNA sequences by means of hybridization inter alia in the manual "The DIG System Users Guide for Filter Hybridization" from Boehringer Mannheim GmbH (Mannheim, Germany, 1993) I.B.R. and in Liebl et al. (International Journal of Systematic Bacteriology (1991) 41: 255–260) I.B.R. The person skilled in the art will find instructions for amplifying DNA sequences by means of the polymerase chain reaction (PCR) inter alia in the textbook by Gait, Oligonucleotide Synthesis: A Practical Approach (IRL Press, Oxford, UK, 1984) I.B.R. and in Newton and Graham: PCR (Spektrum Akademischer Verlag, Heidelberg, Germany, 1994) I.B.R. The person skilled in the art will find guidance in this connection inter alia in Martin et al. (Bio/Technology 5, 137–146 (1987)) I.B.R., in Guerrero et al. (Gene 138, 35–41 (1994)) I.B.R., Tsuchiya and Morinaga (Bio/Technology 6, 428–430 (1988)) I.B.R., in Eikmanns et al. (Gene 102, 93–98 (1991)) I.B.R., in EP 0 472 869 I.B.R., in U.S. Pat. No. 4,601,893 I.B.R., in Schwarzer and Pühler (Bio/Technology 9, 84–87 (1991)), in Reinscheid et al. (Applied and Environmental Microbiology 60, 126–132 (1994)) I.B.R., in LaBarre et al. (Journal of Bacteriology 175, 1001–1007 (1993)) I.B.R., in WO 96/15246 I.B.R., in Malumbres et al. (Gene 134, 15–24 (1993)) I.B.R., in JP-A-10-229891 I.B.R., in Jensen and Hammer (Biotechnology and Bioengineering 58, 191–195 (1998)) I.B.R., in Makrides (Microbiological Reviews 60:512–538 (1996)) I.B.R. and in known textbooks of genetics and molecular biology.

The expert can find additional information on this e.g. in the patent application WO 96/15246 I.B.R., in Boyd and Murphy (Journal of Bacteriology 170: 5949 (1988)) I.B.R., in Voskuil and Chambliss (Nucleic Acids Research 26: 3548 (1998) I.B.R., in Jensen and Hammer (Biotechnology and Bioengineering 58: 191 (1998)) I.B.R., in Pátek et al. (Microbiology 142: 1297 (1996)) I.B.R. and in known textbooks of genetics and molecular biology, such as e.g. the textbook by Knippers ("Molekulare Genetik" [Molecular Genetics], 6th edition, Georg Thieme Verlag, Stuttgart, Germany, 1995) I.B.R. or that by Winnacker ("Gene und Klone" [Genes and Clones], VCH Verlagsgesellschaft, Weinheim, Germany, 1990) I.B.R.

By way of example, the glbO gene according to the invention was over-expressed with the assistance of plasmids.

Suitable plasmids are those which are replicated in coryneform bacteria. Numerous known plasmid vectors, such as for example pZ1 (Menkel et al., Applied and Environmental Microbiology (1989) 64: 549–554) I.B.R., pEKEx1 (Eikmanns et al., Gene 102:93–98 (1991) I.B.R.) or pHS2-1 (Sonnen et al., Gene 107:69–74 (1991) I.B.R.) are based on the cryptic plasmids pHM1519, pBL1 or pGA1. Other plasmid vectors, such as for example those based on pCG4 (U.S. Pat. No. 4,489,160 I.B.R.), or pNG2 (Serwold-Davis et al., FEMS Microbiology Letters 66, 119–124 (1990) I.B.R.), or pAG1 (U.S. Pat. No. 5,158,891 I.B.R.) may be used in the same manner.

Further suitable plasmid vectors are those with the assistance of which gene amplification may be performed by integration into the chromosome, as has for example been described by Reinscheid et al. (Applied and Environmental Microbiology 60, 126–132 (1994)) I.B.R. for the duplication or amplification of the hom-thrB operon. In this method, the complete gene is cloned into a plasmid vector which can replicate in a host (typically E. coli), but not in C. glutamicum. Vectors which may be considered are, for example, pSUP301 (Simon et al., Bio/Technology 1, 784–791 (1983) I.B.R.), pK18mob or pK19mob (Schäfer et al., Gene 145, 69–73 (1994) I.B.R.), pGEM-T (Promega corporation, Madison, Wis., USA), pCR2.1-TOPO (Shuman (1994). Journal of Biological Chemistry 269:32678–84 I.B.R.; U.S. Pat. No. 5,487,993 I.B.R.), pCR® Blunt (Invitrogen, Groningen, Netherlands; Bernard et al., Journal of Molecular Biology, 234: 534–541 (1993) I.B.R.) or pEM1 (Schrumpf et al, 1991, Journal of Bacteriology 173:4510–4516 I.B.R.). The plasmid vector which contains the gene to be amplified is then transferred into the desired strain of C. glutamicum by conjugation or transformation. The conjugation method is described, for example, in Schäfer et al. (Applied and Environmental Microbiology 60, 756–759 (1994)) I.B.R. Transformation methods are described, for example, in Thierbach et al. (Applied Microbiology and Biotechnology 29, 356–362 (1988)) I.B.R., Dunican and Shivnan (Bio/Technology 7, 1067–1070 (1989)) I.B.R. and Tauch et al. (FEMS Microbiological Letters 123, 343–347 (1994)) I.B.R. After homologous recombination by means of "crossing over", the resultant strain contains at least two copies of the gene in question.

The present invention accordingly also provides a process for the fermentative production of L-amino acids, in particular L-lysine, in which a strain transformed with a plasmid vector is used and the plasmid vector bears the nucleotide sequence of the gene which codes for the haemoglobin-like protein.

It may additionally be advantageous for the production of L-amino acids, in particular L-lysine, to amplify not only the glbO gene, but also further genes of the biosynthetic pathway of the desired L-amino acid, such that one or more enzymes of the particular biosynthetic pathway, of glycolysis, of anaplerotic metabolism or of amino acid export is/are over-expressed.

For the production of L-lysine, for example, it is thus possible, in addition to enhancing the glbO gene, simultaneously to enhance, in particular over-express, one or more corynebacterium genes selected from the group the dapA gene, which codes for dihydropicolinate synthase (EP-B 0 197 335 I.B.R.), the gap gene, which codes for glyceraldehyde-3-phosphate dehydrogenase (Eikmanns (1992), Journal of Bacteriology 174:6076–6086 I.B.R.), the tpi gene, which codes for triosephosphate isomerase (Eikmanns (1992), Journal of Bacteriology 174:6076–6086 I.B.R.), the pgk gene, which codes for 3-phosphoglycerate kinase (Eikmanns (1992), Journal of Bacteriology 174:6076–6086 I.B.R.), the pyc gene, which codes for pyruvate carboxylase (Eikmanns (1992), Journal of Bacteriology 174:6076–6086 I.B.R.), and the lysE gene, which codes for lysine export (DE-A-195 48 222 I.B.R.).

It may furthermore be advantageous for the production of amino acids, in particular L-lysine, in addition to amplifying the glbO gene, simultaneously to attenuate, in particular reduce the expression of one or more of the following corynebacterium genes, the pck gene, which codes for phosphoenolpyruvate carboxykinase (DE 199 50 409.1 I.B.R., DSM 13047) and/or the pgi gene, which codes for glucose 6-phosphate isomerase (U.S. Ser. No. 09/396,478 I.B.R., DSM 12969), the poxB gene, which codes for pyruvate oxidase (DE: 199 51 975.79 I.B.R.).

It may furthermore be advantageous for the production of L-amino acids, in particular L-lysine, in addition to over-expressing the glbO gene, to suppress unwanted secondary reactions (Nakayama: "Breeding of Amino Acid Producing Micro-organisms", in: Overproduction of Microbial Products, Krumphanzl, Sikyta, Vanek (eds.), Academic Press, London, UK, 1982 I.B.R.).

For the purposes of amino acid production, in particular of L-lysine, the microorganisms produced according to the invention may be cultured continuously or discontinuously using the batch process or the fed batch process or repeated fed batch process. A summary of known culture methods is given in the textbook by Chmiel (Bioprozesstechnik 1. Einf ührung in die Bioverfahrenstechnik (Gustav Fischer Verlag, Stuttgart, 1991) I.B.R.) or in the textbook by Storhas (Bioreaktoren und periphere Einrichtungen (Vieweg Verlag, Braunschweig/Wiesbaden, 1994)) I.B.R.

The culture medium to be used must adequately satisfy the requirements of the particular strains. Culture media for various microorganisms are described in "Manual of Methods for General Bacteriology" from the American Society for Bacteriology (Washington D.C., USA, 1981) I.B.R. Carbon sources which may be used include sugars and carbohydrates, such as for example glucose, sucrose, lactose, fructose, maltose, molasses, starch and cellulose, oils and fats, such as for example soya oil, sunflower oil, peanut oil and coconut oil, fatty acids, such as for example palmitic acid, stearic acid and linoleic acid, alcohols, such as for example glycerol and ethanol, and organic acids, such as for example acetic acid. These substances may be used individually or as a mixture. Nitrogen sources which may be used comprise organic compounds containing nitrogen, such as peptones, yeast extract, meat extract, malt extract, corn steep liquor, soya flour and urea or inorganic compounds, such as ammonium sulfate, ammonium chloride, ammonium phosphate, ammonium carbonate and ammonium nitrate. The nitrogen sources may be used individually or as a mixture. Phosphorus sources which may be used are phosphoric acid, potassium dihydrogen phosphate or dipotassium hydrogen phosphate or the corresponding salts containing sodium. The culture medium must additionally contain salts of metals, such as magnesium sulfate or iron sulfate for example, which are necessary for growth. Finally, essential growth-promoting substances such as amino acids and vitamins may also be used in addition to the above-stated substances. Suitable precursors may furthermore be added to the culture medium. The stated feed substances may be added to the culture as a single batch or be fed appropriately during culturing.

Basic compounds, such as sodium hydroxide, potassium hydroxide, ammonia or ammonia water, or acidic compounds, such as phosphoric acid or sulfuric acid, are used appropriately to control the pH of the culture. Foaming may be controlled by using antifoaming agents such as fatty acid polyglycol esters for example. Plasmid stability may be maintained by the addition to the medium of suitable selectively acting substances, for example antibiotics. Oxygen or oxygen-containing gas mixtures, such as air for example, are introduced into the culture in order to maintain aerobic conditions. The temperature of the culture is normally from 20° C. to 45° C. and preferably from 25° C. to 40° C. The culture is continued until the maximum quantity of L-lysine has formed. This aim is normally achieved within 10 to 160 hours.

The present invention accordingly provides a process for the fermentative production of L-amino acids, in particular L-lysine, in which the following steps are performed:

a) fermentation of the L-amino acid producing coryneform bacteria in which at least the glbO gene which codes for the haemoglobin-like protein is enhanced, in particular over-expressed.

b) accumulation of the L-amino acid in the medium or in the cells of the bacteria and c) isolation of the L-amino acid.

Analysis of L-lysine may be performed by anion exchange chromatography with subsequent ninhydrin derivation, as described in Spackinan et al. (Analytical Chemistry, 30, (1958), 1190) I.B.R.

The purpose of the process according to the invention is the fermentative production of L-amino acids, in particular L-lysine.

EXAMPLES

The present invention is illustrated in greater detail by the following practical examples.

Example 1

Production of a genomic cosmid gene library from *Corynebacterium glutamicum* ATCC 13032

Chromosomal DNA from Corynebacterium glutamicum ATCC 13032 was isolated as described in Tauch et al., (1995, Plasmid 33:168–179) I.B.R. and partially cleaved with the restriction enzyme Sau3AI (Amersham Pharmacia, Freiburg, Germany, product description Sau3AI, code no. 27-0913-02) I.B.R. The DNA fragments were dephosphorylated with shrimp alkaline phosphatase (Roche Molecular Biochemicals, Mannheim, Germany, product description SAP, code no. 1758250). The DNA of cosmid vector Super-Cos1 (Wahl et al. (1987) Proceedings of the National Academy of Sciences USA 84:2160–2164 I.B.R.), purchased from Stratagene (La Jolla, USA, product description SuperCos1 Cosmid Vector Kit, code no. 251301) was cleaved with the restriction enzyme XbaI (Amersham Pharmacia, Freiburg, Germany, product description XbaI, code no. 27-0948-02) and also dephosphorylated with shrimp alkaline phosphatase. The cosmid DNA was then cleaved with the restriction enzyme BamHI (Amersham Pharmacia, Freiburg, Germany, product description BamHI, code no. 27-0868-04). Cosmid DNA treated in this manner was mixed with the treated ATCC 13032 DNA and the batch was treated with T4 DNA ligase (Amersham Pharmacia, Freiburg, Germany, product description T4 DNA Ligase, code no. 27-0870-04). The ligation mixture was then packed in phages using Gigapack II XL Packing Extracts (Stratagene, La Jolla, USA, product description Gigapack II XL Packing Extract, code no. 200217). *E. coli* strain NM554 (Raleigh et al. 1988, Nucleic Acid Res. 16:1563–1575 I.B.R.) was infected by suspending the cells in 10 mM $MgSO_4$ and mixing them with an aliquot of the phage suspension. The cosmid library was infected and titred as described in Sambrook et al. (1989, Molecular Cloning: A laboratory Manual, Cold Spring Harbor) I.B.R., the cells being plated out on LB agar (Lennox, 1955, Virology, 1:190) with 100 µg/ml of ampicillin. After overnight incubation at 37° C., individual recombinant clones were selected.

Example 2

Isolation and sequencing of the glbO gene

Cosmid DNA from an individual colony was isolated in accordance with the manufacturer's instructions using the Qiaprep Spin Miniprep Kit (product no. 27106, Qiagen, Hilden, Germany) and partially cleaved with the restriction enzyme Sau3AI (Amersham Pharmacia, Freiburg, Germany, product description Sau3AI, product no. 27-0913-02). The DNA fragments were dephosphorylated with shrimp alkaline phosphatase (Roche Molecular Biochemicals, Mannheim, Germany, product description SAP, product no. 1758250). Once separated by gel electrophoresis, the cosmid fragments of a size of 1500 to 2000 bp were isolated using the QiaExII Gel Extraction Kit (product no. 20021, Qiagen, Hilden, Germany).

The DNA of the sequencing vector pZero-1 purchased from Invitrogen (Groningen, Netherlands, product description Zero Background Cloning Kit, product no. K2500-01) was cleaved with the restriction enzyme BamHI (Amersham Pharmacia, Freiburg, Germany, product description BamHI, product no. 27-0868-04). Ligation of the cosmid fragments into the sequencing vector pZero-1 was performed as described by Sambrook et al. (1989, Molecular Cloning: A Laboratory Manual, Cold Spring Harbor) I.B.R., the DNA mixture being incubated overnight with T4 ligase (Pharmacia Biotech, Freiburg, Germany). This ligation mixture was then electroporated into the E. coli strain DH5αMCR (Grant, 1990, Proceedings of the National Academy of Sciences U.S.A., 87:4645–4649 I.B.R.) (Tauch et al. 1994, FEMS Microbiol Letters, 123:343–7 I.B.R.) and plated out onto LB agar (Lennox, 1955, Virology, 1:190 I.B.R.) with 50 µg/ml of Zeocin.

Plasmids of the recombinant clones were prepared using the Biorobot 9600 (product no. 900200, Qiagen, Hilden, Germany I.B.R.). Sequencing was performed using the dideoxy chain termination method according to Sanger et al. (1977, Proceedings of the National Academy of Sciences U.S.A., 74:5463–5467 I.B.R.) as modified by Zimmermann et al. (1990, Nucleic Acids Research, 18:1067) I.B.R. The "RR dRhodamin Terminator Cycle Sequencing Kit" from PE Applied Biosystems (product no. 403044, Weiterstadt, Germany) was used. Separation by gel electrophoresis and analysis of the sequencing reaction was performed in a "Rotiphorese NF" acrylamide/bisacrylamide gel (29:1) (product no. A124.1, Roth, Karlsruhe, Germany) using the "ABI Prism 377" sequencer from PE Applied Biosystems (Weiterstadt, Germany).

The resultant raw sequence data were then processed using the Staden software package (1986, Nucleic Acids Research, 14:217–231 I.B.R.), version 97-0. The individual sequences of the pZero1 derivatives were assembled into a cohesive contig. Computer-aided coding range analysis was performed using XNIP software (Staden, 1986, Nucleic Acids Research, 14:217–231) I.B.R. Further analysis was performed using the "BLAST search programs" (Altschul et al., 1997, Nucleic Acids Research, 25:3389–3402 I.B.R.), against the non-redundant database of the "National Center for Biotechnology Information" (NCBI, Bethesda, Md., USA).

The resultant nucleotide sequence is stated in SEQ ID no. 1. Analysis of the nucleotide sequence revealed an open reading frame of 393 base pairs, which was designated the glbO gene. The glbO gene codes for a protein of 131 amino acids.

Example 3

Production of a shuttle vector pEC-K18mob2glbOexp for enhancing the glbO gene in C. glutamicum 3.1 Production of the E. coli-C. glutamicum shuttle vector pEC-K18mob2

The E. coli-C. glutamicum shuttle vector was constructed in accordance with the prior art. The vector contains the replication region rep of plasmid pGA1, including the replication effector per (U.S. Pat. No. 5,175,108 I.B.R.; Nesvera et al., Journal of Bacteriology 179, 1525–1532 (1997) I.B.R.), the aph(3')-IIa gene of transposon Tn5, which imparts kanamycin resistance (Beck et al., Gene 19, 327–336 (1982) I.B.R.), the replication region oriV of plasmid pMB1 (Sutcliffe, Cold Spring Harbor Symposium on Quantitative Biology 43, 77–90 (1979) I.B.R.), the lacZα gene fragment including the lac promoter and a multiple cloning site (mcs) (Norrander, J. M. et al., Gene 26, 101–106 (1983) I.B.R.) and the mob region of plasmid RP4 (Simon et al., Bio/Technology 1:784–791 (1983) I.B.R.). The constructed vector was then transformed into E. coli strain DH5α (Hanahan, in: DNA Cloning. A Practical Approach. Vol. I. IRL-Press, Oxford, Washington D.C., USA I.B.R.).

Plasmid-bearing cells were selected by plating the transformation batch out onto LB agar (Sambrook et al., Molecular Cloning: A Laboratory Manual. $2^{nd}$ Ed. Cold Spring Harbor Laboratory Press, Cold Spring Harbor, N.Y. I.B.R.) which had been supplemented with 25 mg/l of kanamycin. Plasmid DNA was isolated from a transformant using the QIAprep Spin Miniprep Kit from Qiagen and verified by restriction with the restriction enzymes EcoRI and HindIII and subsequent agarose gel electrophoresis (0.8%). The plasmid was named pEC-K18mob2 and is shown in FIG. 1.

The following microorganism has been deposited on Jan. 20, 2000 with Deutsche Sammlung für Mikroorganismen und Zellkulturen (DSMZ, Braunschweig, Germany) in accordance with the Budapest Treaty:

C. glutamicum strain DSM 5715/pEC-K18mob2 as DSM 13245

3.2. Cloning of glbO in the E. coli-C. glutamicum shuttle vector pEC-K18mob2

The vector used was the E. coli-C. glutamicum shuttle vector pEC-K18mob2 described in Example 3.1. DNA from this plasmid was completely cleaved with the restriction enzyme Ecl136II and then dephosphorylated with shrimp alkaline phosphatase (Roche Diagnostics GmbH, Mannheim, Germany, product description SAP, product no. 1758250).

Chromosomal DNA was isolated from strain ATCC 13032 using the method of Eikmanns et al. (Microbiology 140: 1817–1828 (1994)). On the basis of the sequence of the glbO gene for C. glutamicum known from Example 2, the following oligonucleotides were selected for the polymerase chain reaction:

glb-exp1 shown in SEQ ID no. 3
    5' GGT CGG TGA GAT AAT CAG 3'
glb-exp2 shown in SEQ ID no. 4
    5' TGG CAG AAG TTA AGC GTG 3'

The stated primers were synthesized by the company ARK Scientific GmbH Biosystems (Darmstadt, Germany) and the PCR reaction performed in accordance with the standard PCR method of Innis et al. (PCR Protocols. A Guide to Methods and Applications, 1990, Academic Press I.B.R.) using Pwo polymerase from Roche Diagnostics GmbH (Mannheim, Germany). By means of the polymerase chain reaction, the primers permit the amplification of a 936 kb DNA fragment, which bears the glbO gene.

The glbO fragment obtained in this manner was mixed with the prepared pEC-K18mob2 vector and the batch was treated with T4 DNA ligase (Amersham Pharmacia, Freiburg, Germany, product description T4 DNA Ligase, code no. 27-0870-04). The ligation batch was then transformed into E. coli strain DH5α (Hanahan, in: DNA cloning. A Practical Approach. Vol. 1. IRL-Press, Oxford, Washington D.C., USA I.B.R.). Plasmid-bearing cells were selected by plating the transformation batch out onto LB agar (Lennox, 1955, Virology, 1:190 I.B.R.) with 25 mg/l of kanamycin. After overnight incubation at 37° C., individual recombinant clones were selected. Plasmid DNA was isolated from a transformant in accordance with the manufacturer's instructions using the Qiaprep Spin Miniprep Kit (product no. 27106, Qiagen, Hilden, Germany) and cleaved with the restriction enzymes EcoRI and EcoRI/PstI in order to check the plasmid by subsequent agarose gel electrophoresis. The DNA sequence of the amplified DNA fragment was checked by sequencing. The resultant plasmid was named pEC-K18mob2glbOexp. It is shown in FIG. 2.

Example 4

Transformation of strain DSM5715 with plasmid pEC-K18mob2glbOexp

Strain DSM5715 was then transformed with plasmid pEC-K18mob2glbOexp using the electroporation method described by Liebl et al. (FEMS Microbiology Letters, 53:299–303 (1989)) I.B.R. Transformant selection proceeded on LBHIS agar consisting of 18.5 g/l of brain-heart infusion bouillon, 0.5 M sorbitol, 5 g/l of Bacto tryptone, 2.5 g/l of Bacto yeast extract, 5 g/l of NaCl and 18 g/l of Bacto agar, which had been supplemented with 25 mg/l of kanamycin. Incubation was performed for 2 days at 33° C.

Plasmid DNA was isolated from a transformant using the conventional methods (Peters-Wendisch et al., 1998, Microbiology, 144, 915–927 I.B.R.), cut with the restriction endonucleases EcoRI and EcoRI/PstI and the plasmid was checked by subsequent agarose gel electrophoresis. A pure culture of the strain was named DSM5715/pEC-K18mob2glbOexp.

Example 5

Production of lysine

The *C. glutamicum* strain DSM5715/pEC-K18mob2glbOexp obtained in Example 4 was cultured in a nutrient medium suitable for the production of lysine and the lysine content of the culture supernatant was determined.

To this end, the strain was initially incubated for 24 hours at 33° C. on an agar plate with the appropriate antibiotic (brain/heart agar with kanamycin (25 mg/l)). Starting from this agar plate culture, a preculture was inoculated (10 ml of medium in a 100 ml Erlenmeyer flask). The complete medium CgIII was used as the medium for this preculture.

| Medium Cg III | |
|---|---|
| NaCl | 2.5 g/l |
| Bacto peptone | 10 g/l |
| Bacto yeast extract | 25 g/l |
| Glucose (separately autoclaved) | 2% (w/v) |
| The pH value was adjusted to pH 7.4. | |

Kanamycin (25 mg/l) was added to this medium. The preculture was incubated for 16 hours at 33° C. on a shaker at 240 rpm. A main culture was inoculated from this preculture, such that the initial OD (660 nm) of the main culture was 0.05. Medium MM was used for the main culture.

| Medium MM | |
|---|---|
| CSL (Corn Steep Liquor) | 5 g/l |
| MOPS (morpholinopropanesulfonic acid) | 20 g/l |
| Glucose (separately autoclaved) | 50 g/l |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| L-leucine (sterile-filtered) | 0.1 g/l |
| $CaCO_3$ | 25 g/l |

CSL, MOPS and the salt solution were adjusted to pH 7 with ammonia water and autoclaved. The sterile substrate and vitamin solutions, together with the dry-autoclaved $CaCO_3$ are then added.

Culturing is performed in a volume of 10 ml in a 100 ml Erlenmeyer flask with flow spoilers. Kanamycin (25 mg/l) was added. Culturing was performed at 33° C. and 80% atmospheric humidity.

After 72 hours, the OD was determined at a measurement wavelength of 660 nm using a Biomek 1000 (Beckmann Instruments GmbH, Munich). The quantity of lysine formed was determined using an amino acid analyzer from Eppendorf-BioTronik (Hamburg, Germany) by ion exchange chromatography and post-column derivation with ninhydrin detection.

Table 1 shows the result of the test.

TABLE 1

| Strain | OD (660 nm) | Lysine HCl 25 g/l |
|---|---|---|
| DSM5715 | 7.6 | 13.5 |
| DSM5715/pEC-K18mob2glbOexp | 8.5 | 15.7 |

What is claimed is:

1. A method for the producing of L-amino acids, comprising:
culturing coryneform bacteria, which include an overexpressed globin oxygen (glbO) gene having the polynucleotide sequence of SEQ ID NO: 1, in a medium suitable for the expression of the glbO to thereby produce L-amino acids.

2. The method according to claim 1, further comprising:
accumulating the L-amino acids in the medium or in cells of the bacteria.

3. The method according to claim 2, further comprising:
isolating the L-amino acids.

4. The method according to claim 1, wherein the bacteria have been transformed with a plasmid vector which comprises the nucleotide sequence of SEQ ID NO: 1.

5. The method according to claim 1, wherein the coryneform bacteria produce L-lysine.

6. The method according to claim 1, wherein the bacteria further include one or more overexpressed corynebacterium gene selected from the group consisting of:
the dapA gene, which codes for dihydropicolinate synthase,
the pyc gene, which codes for pyruvate carboxylase,
the tpi gene, which codes for triosephosphate isomerase,
the gap gene, which codes for glyceraldehyde 3-phosphate dehydrogenase,
the pgk gene, which codes for 3-phosphoglycerate kinase, and
the lysE gene, which codes for lysine export.

7. The method according to claim 1, wherein the bacteria further include one or more attenuated corynebacterium gene selected from the group consisting of:
the pck gene, which codes for phosphoenolpyruvate carboxykinase,
the pgi gene, which codes for glucose 6-phosphate isomerase, and
the poxB gene, which codes for pyruvate oxidase.

8. A method according to claim 1, wherein the bacteria are Corynebacterium glutamicum.

9. The process for producing L-amino acids, comprising:
culturing coryneform bacteria, which include an overexpresssed polynucleotide sequence that includes nucleotides 186 to 578 of SEQ ID NO: 1 in a medium suitable for the expression of said polynucleotide.

10. A process for producing L-amino acids comprising:
a) transforming a Coryneform bacterium with a vector which includes a globin oxygen (glbO) gene having the polynucleotide sequence of SEQ ID NO: 1, wherein said glbO gene is under the control of a promoter which allows the overexpression of said glbO gene;
b) culturing said bacteria in a medium suitable for expression of the glbO gene to thereby produce L-amino acids; and
c) isolating the L-amino acids.

11. The process of claim 10 wherein the vector is DSM 5715/pEC-K18mob2.

12. A vector DSM 5715/pEC-K18mob2 deposited under the number DSM 13245.

13. A method for producing L-amino acids, comprising:
culturing coryneform bacteria, which include an overexpressed globin oxygen (glbO) gene having a polynucleotide sequence which encodes the amino acid sequence of SEQ ID NO: 2, in a medium suitable for the expression of the glbO to thereby produce L-amino acids.

14. The method according to claim 13, further comprising:
accumulating the L-amino acids in the medium or in cells of the bacteria.

15. The method according to claim 14, further comprising:

isolating the L-amino acids.

16. The method according to claim 13, wherein the bacteria have been transformed with a plasmid vector which comprises the nucleotide sequence of SEQ ID NO: 1.

17. The method according to claim 13, wherein the coryneform bacteria produce L-lysine.

18. The method according to claim 13, wherein the bacteria further include one or more overexpressed corynebacterium gene selected from the group consisting of:

the dapA gene, which codes for dihydropicolinate synthase, the pyc gene, which codes for pyruvate carboxylase, the tpi gene, which codes for triosephosphate isomerase, the gap gene, which codes for glyceraldehyde 3-phosphate dehydrogenase, the pgk gene, which codes for 3-phosphoglycerate kinase, and the lysE gene, which codes for lysine export.

19. The method according to claim 13, wherein the bacteria further include one or more attenuated corynebacterium gene selected from the group consisting of:

the pck gene, which codes for phosphoenolpyruvate carboxykinase, the pgi gene, which codes for glucose 6-phosphate isomerase, and the poxB gene, which codes for pyruvate oxidase.

20. A method according to claim 13, wherein the bacteria are Corynebacterium glutamicum.

* * * * *

SEQUENCE LISTING

<160> NUMBER OF SEQ ID NOS: 4

<210> SEQ ID NO 1
<211> LENGTH: 840
<212> TYPE: DNA
<213> ORGANISM: Corynebacterium glutamicum
<220> FEATURE:

```
<221> NAME/KEY: CDS
<222> LOCATION: (186)..(578)
<223> OTHER INFORMATION:

<400> SEQUENCE: 1
atggtggttt taccggcgcc atttggacca agtacggccc agtgcgaccc ttgcggaatt      60
gagagggaga tatcgtcgag aagcaatttc tcgccgcgcc gcacggtgac gccggccatg     120
ttgagtgcta gttcgcgcat gggtaacacc ttactgcgt aaggccaggg cttagactgg      180 taccc atg aca acc tca gaa aat ttt tat gat tct gtg ggc ggc gag gaa      230
      Met Thr Thr Ser Glu Asn Phe Tyr Asp Ser Val Gly Gly Glu Glu
      1               5                   10                  15 acg ttt tcc ctc atc gtc cac cgt ttt tat gaa cag gtc ccc aac gac        278
Thr Phe Ser Leu Ile Val His Arg Phe Tyr Glu Gln Val Pro Asn Asp
            20                  25                  30 gat att tta ggc ccg atg tat ccg ccg gat gat ttt gag ggc gcc gag        326
Asp Ile Leu Gly Pro Met Tyr Pro Pro Asp Asp Phe Glu Gly Ala Glu
        35                  40                  45 cag cgt cta aag atg ttc ctc agc cag tac tgg ggc ggc ccg aag gat        374
Gln Arg Leu Lys Met Phe Leu Ser Gln Tyr Trp Gly Gly Pro Lys Asp
    50                  55                  60 tat cag gag cag cgt gga cac cct cgt ctg cgc atg cgt cac gtc aat        422
Tyr Gln Glu Gln Arg Gly His Pro Arg Leu Arg Met Arg His Val Asn
65                  70                  75 tac ccc atc ggc gtc acc gca gcg gag cgt tgg ctg cag ctc atg tcc        470
Tyr Pro Ile Gly Val Thr Ala Ala Glu Arg Trp Leu Gln Leu Met Ser
80                  85                  90                  95 aat gca ctc gac ggc gtg gat ttg acc gcg gag cag cgt gaa gcg att        518
Asn Ala Leu Asp Gly Val Asp Leu Thr Ala Glu Gln Arg Glu Ala Ile
                100                 105                 110 tgg gag cat atg gtg cgc gcg gcc gat atg ctg atc aat tcc aac ccc        566
Trp Glu His Met Val Arg Ala Ala Asp Met Leu Ile Asn Ser Asn Pro
            115                 120                 125 gat ccg cac gct taacttctgc caaaaagtcg ttttgaccat aagctaagcg            618
Asp Pro His Ala
        130 attgtgaatc gaattgcaga atcgcacgc agtttcggcg tgctgggctt cagcgctttc       678 ggcggcccca ccgcgcacct cggatatttc cgcacggaat tcgtggagcg gcggcgctgg     738 ctggatgatc gccaatattc cgagatcgta gcgctcagcc aactacttcc cggacctgga     798 tcgtcgcagg tcggtatgat gctgggctac caccgcgccg gt                        840

<210> SEQ ID NO 2
<211> LENGTH: 131
<212> TYPE: PRT
<213> ORGANISM: Corynebacterium glutamicum

<400> SEQUENCE: 2

Met Thr Thr Ser Glu Asn Phe Tyr Asp Ser Val Gly Gly Glu Glu Thr
1               5                   10                  15

Phe Ser Leu Ile Val His Arg Phe Tyr Glu Gln Val Pro Asn Asp Asp
            20                  25                  30

Ile Leu Gly Pro Met Tyr Pro Pro Asp Asp Phe Glu Gly Ala Glu Gln
        35                  40                  45

Arg Leu Lys Met Phe Leu Ser Gln Tyr Trp Gly Gly Pro Lys Asp Tyr
    50                  55                  60

Gln Glu Gln Arg Gly His Pro Arg Leu Arg Met Arg His Val Asn Tyr
65                  70                  75                  80
```

```
Pro Ile Gly Val Thr Ala Ala Glu Arg Trp Leu Gln Leu Met Ser Asn
            85                  90                  95

Ala Leu Asp Gly Val Asp Leu Thr Ala Glu Gln Arg Glu Ala Ile Trp
            100             105                 110

Glu His Met Val Arg Ala Ala Asp Met Leu Ile Asn Ser Asn Pro Asp
        115                 120                 125

Pro His Ala
    130

<210> SEQ ID NO 3
<211> LENGTH: 18
<212> TYPE: DNA
<213> ORGANISM: Corynebacterium glutamicum

<400> SEQUENCE: 3
ggtcggtgag ataatcag                                                    18

<210> SEQ ID NO 4
<211> LENGTH: 18
<212> TYPE: DNA
<213> ORGANISM: Corynebacterium glutamicum

<400> SEQUENCE: 4
tggcagaagt taagcgtg                                                    18
```